United States Patent [19]
Dreyer

[11] Patent Number: 5,597,809
[45] Date of Patent: Jan. 28, 1997

[54] TREATMENT OF OPTIC NEURITIS

[75] Inventor: Evan B. Dreyer, Chestnut Hill, Mass.

[73] Assignee: Massachusetts Eye & Ear Infirmary, Boston, Mass.

[21] Appl. No.: 264,728

[22] Filed: Jun. 23, 1994

[51] Int. Cl.$^6$ ............................................. A01N 43/04
[52] U.S. Cl. .................. 514/37; 514/145; 514/148; 514/224.8; 514/231.2; 514/233.2; 514/256; 514/260; 514/277; 514/278; 514/299; 514/312; 514/314; 514/317; 514/345; 514/469; 514/492; 514/493; 514/498; 514/501; 514/504; 514/530; 514/601; 514/602; 514/608; 514/613; 514/616; 514/646; 514/647
[58] Field of Search .................................. 514/912, 913, 514/914, 915, 233.2, 317, 662, 37, 145, 148, 224.8, 231.2, 256, 260, 277, 278, 299, 312, 314, 345, 469, 492, 493, 498, 501, 504, 530, 601, 602, 608, 613, 616, 646, 447, 664, 665, 706, 707, 724, 731, 734, 744, 745, 757, 759, 764; 546/72, 192; 564/549

[56] References Cited

FOREIGN PATENT DOCUMENTS

WO88/05306  7/1988  WIPO .

OTHER PUBLICATIONS

Levy et al, Neuralogy, vol. 40, #5, pp. 852–855, 1990.
Chemical Abstracts, vol. 119, #3 p. 75, 1993, 203a8.
Fraunfelder et al., Journal of Toxicology 13:311–316, 1994.
Pellegrini et al., Annals of Neurology 33:403–407, 1993.
Campbell, I. A., et al., "Ethambutol and the Eye", 1988, *Letter: The Lancet*, 2(8601):113–14.
Choi, D. W., et al., "Glutamate Neurotoxicity, Calcium, and Zinc$^{\alpha}$", 1989, Annals NY Acad. Sci., 568:219–24.
Christine, C. W., et al., "Effect of Zinc on NMDA Receptor–Mediated Channel Current in Cortical Neurons", 1990, *J. Neuroscience*, 10(1):108–16.

Dreyer, E. B., et al., "Greater Sensitivity of Larger Retinal Ganglion Cells to NMDA–mediated Cell Death", 1994, *Neuroreport*, 5(5):629–31.
Dreyer, E. B., et al., "HIV–1 Coat Protein Neurotoxicity Prevented by Calcium Channel Antagonists", 1990, *Science*, 248:364–67.
Elo, R., et al., "Serum Iron, Copper, Magnesium and Zinc Concentration in Chronic Pulmonary Tuberculosis during Chemotherapy with Capreomycin–Ethambutol–Rifampicin Combinations", 1970, *Scand. J. Resp. Dis.*, 51:249–55.
Figueroa, R., et al., "Effect of Ethambutol on the Ocular Zinc Concentration in Dogs", 1971, *Am. Rev. of Respiratory Disease*, 104(4):592–94.
Hahn, J. S., et al., "Central Mammalian Neurons Normally Resistant to Glutamate Toxicity are Made Sensitive by Elevated Extracellular Ca$^{2+}$: Toxicity is Blocked by the N–methyl–D–aspartate Antagonist MK–801", 1988, *Proc. Natl. Acad. Sci. USA*, 85:6556–60.
Joubert, P. H., et al., "Subclinical Impairment of Colour Vision in Patients Receiving Ethambutol", 1986, *Br. J. Clin. Pharmac.*, 21:213–16.
Kahana, L. M., "Ethambutol and the Eye", 1988, *Letters: The Lancet*, p. 627.
Kakisu, Y., et al., "Pattern Electroetinogram and Visual Evoked Cortical Potential in Ethambutol Optic Neuropathy", 1988, *Documenta Ophthalmologica*, 67:327–34.
Levy, D. I., et al., "Comparison of Delayed Administration of Competitive and Uncompetitive Antagonists in Preventing NMDA Receptor–mediated Neuronal Death", 1990, *Neurology*, 40(5):852–55.

(List continued on next page.)

Primary Examiner—Gary Geist
Assistant Examiner—Deborah D. Carr
Attorney, Agent, or Firm—Fish & Richardson, P.C.

[57] ABSTRACT

Methods of treating optic neuritis comprising administering a protective agent which inhibits glutamate-mediated retinal cell damage to a mammal at risk of developing optic neuritis.

7 Claims, 6 Drawing Sheets

OTHER PUBLICATIONS

Levy, D. I., et al., "Redox Modulation of NMDA Receptor-mediated Toxicity in Mammalian Central Neurons", 1990, *Neuroscience Letters*, 110:291–96.

Lipton, S. A., et al., "Mechanisms of Disease", 1994, *N. Eng. J. Med.*, 330(9):613–22.

Lucas, D. R., et al., "The Toxic Effect of Sodium L–Glutamate on the Inner Layers of the Retina", 1957, *AMA Archives, Ophthalmology*, 58(1):193–201.

Olney, J. W., "Glutamate–Induced Retinal Degeneration in Neonatal Mice. Electron Microscopy of the Acutely Evolving Lesion", 1969, *J. Neuropathology and Experimental Neurology*, 28:455–74.

Petrera, J. E., et al., "Serial Pattern Evoked Potential Recording in a Case of Toxic Optic Neuropathy Due to Ethambutol", 1988, *Electroencephalography and Clin. Neurophysiology*, 71:146–49.

Sucher, N. J., et al., "N–methyl–D–aspartate Antagonists Prevent Kainate Neurotoxicity in Rat Retinal Ganglion Cells In Vitro", 1991, *J. Neuroscience*, 11(4):966–71.

Sucher, N. J., et al., "Calcium Channel Antagonists Attenuate NMDA Receptor–mediated Neruotoxicity of Retinal Ganglion Cells in Culture", 1991, *Brain Research*, 551:297–302.

Weiss, J. H., et al., "The Calcium Channel Blocker Nifedipine Attenuates Slow Excitatory Amino Acid Neurotoxicity", 1990, *Science*, 247:1474–77.

Yeh, G., et al., "Evidence that Zinc Inhibits N–Methyl–D–Aspartate Receptor–Gated Ion Channel Activation by Noncompetitive Antagonism of Glycine Binding", 1990, *Molecular Pharmacology*, 38(1):14–19.

TREATMENT OF OPTIC NEURITIS

STATEMENT AS TO FEDERALLY SPONSORED RESEARCH

This invention was made with Government support under K08 01395 and R01-10009 awarded by the National Institutes of Health. The Government therefore has certain rights in the invention.

BACKGROUND OF THE INVENTION

The invention relates to optic neuritis.

Ethambutol is an essential drug in the management of mycobacterial infections. Ethambutol, a water-soluble and heat-stable compound, is active against nearly all strains of *M. tuberculosis* and *M. kansasii* as well as many strains of *M. avium* complex. It has no effect on other bacteria. Ethambutol suppresses the growth of most isoniazid-and streptomycin-resistant tubercle bacilli. This drug has few side effects, with the unfortunate exception of optic neuropathy. This can develop in up to 15% of patients taking ethambutol. Ethambutol can lead directly to a decline in visual acuity, the loss of the ability to differentiate red from green, the development of a central scotoma on visual field testing, or the development of concentric constriction of the visual field. In many cases, ethambutol-associated visual impairment is reversible. However, visual loss can be permanent in up to 3% of patients taking ethambutol.

The recent outbreaks of multidrug-resistant (MDR) TB pose an urgent public health problem and require rapid intervention. As a result of the increasing prevalence of drug-resistant TB in the United States, approaches to treatment of tuberculosis have changed. An initial four-drug regimen is now recommended for the treatment of TB. Treatment with the antibiotic, ethambutol, is favored as primary therapy for all newly diagnosed cases. Given the critical role played by ethambutol in the management of mycobacterial infections in both the general population and the AIDS-infected population, the potentially devastating visual loss that may result as a consequence of ethambutol therapy assumes great significance.

Although visual impairment and visual loss as a result of treatment with ethambutol and other agents has been well-documented, the mechanism by which the damage occurs has not been described.

SUMMARY OF THE INVENTION

The invention is based on the discovery by the inventors of a process which is important in the etiology of optic neuritis. Accordingly, the invention provides methods of treating optic neuritis and visual impairment in mammals at risk of developing optic neuritis by administering a protective agent which inhibits glutamate-mediated retinal cell damage.

The claimed methods may be used to treat optic neuritis that is idiopathic or induced by drugs. Mammals at risk of developing optic neuritis are defined as those which are undergoing treatment with a drug, or suffering from a disease state or condition known to cause or being suspected of causing visual impairment or loss, particularly where, because other diseases affecting the eye have been ruled out, optic neuritis is a possible or likely cause of the visual loss. For example, a number of drugs have been shown to cause toxic optic neuropathy (see Table 13). Although non-drug-induced optic neuritis is generally idiopathic, its occurence is more common in young females and patients with multiple sclerosis.

The inventor's discovery that optic neuritis associated with certain drugs is mediated through the N-Methyl-D-aspartate (NMDA) receptor gave rise to the recognition that NMDA antagonists can protect retinal ganglion cells. Thus, a second aspect of the invention features a method of reducing drug toxicity in a mammal by administering a drug either concurrently or sequentially with a protective agent which inhibits glutamate-mediated retinal cell damage. Protective agents can act either by reducing the functional impairment of optic nerve cells or their destruction. The drug administered with the protective agent may be any substance suspected of causing damage to optic nerve cells, e.g. retinal ganglion cells. Examples are antibiotics, e.g., ethambutol which, is a drug used to treat mycobacterial infections such as tuberculosis. The antibiotic should be one which remains chemotherapeutically active in the presence of the protective agent.

Preferred protective agents are NMDA antagonists such as uncompetitive open channel blocking agents, e.g, memantine or dizocilpine (MK-801). Other uncompetitive NMDA antagonists are, e.g., derivatives of dibenzyocycloheptene (Merck; Somerset, N.J.), sigma receptor ligands, e.g., dextrorphan, dextromethorphan and morphinan derivatives (Hoffman LaRoche; Nutley, N.J.), such as caramiphen and rimcazole (which also block calcium channels), Ketamine, Tiletamine and other cyclohexanes, Phencyclidine (PCP) and derivatives, pyrazine compounds, amantadine, rimantadine and derivatives, CNS 1102 (and related bi-and tri-substituted guanidines), diamines, Conantokan peptide from Conus geographus, and Agatoxin-489.

The protective agent may also be a competitive NMDA receptor binding agent, i.e., an agent which acts at the agonist binding site, e.g., CGS-19755 (CIBA-GEIGY; Summit, N.J.) and other piperdine derivatives, D-2-amino-7-phosphonoheptanoate (AP7), CPP {[3-(2-carboxypiperazin-4-y-propyl-1-phosphonic acid)]}, LY 274614, CGP39551, CGP37849, LY233053, LY233536, O-phosphohomoserine, or MDL100-453. A preferred competitive NMDA receptor binding agent is 2-amino-5-phosphonovalerate (APV).

Other NMDA antagonists that can be used in the claimed methods include NMDA antagonists which are active at the glycine site of the NMDA receptor, e.g., Kynurenate, 7-chloro-kynurenate, 5,7-chloro-kynurenate, thio-derivatives, and other derivatives (Merck), indole-2-carboxylic acid, DNQX, Quinoxaline or oxidiazole derivatives including CNQX, NBQX, Glycine partial agonist (e.g., P-9939, Hoecht-Roussel; Somerville, N.J.). Also included are NMDA antagonists which are active at the polyamine site of the NMDA receptor: Arcaine and related biguanidines and biogenic polyamines, Ifenprodil and related drugs, Diethylenetriamine SL 82,0715, or 1,10-diaminodecane and related inverse agonists; and NMDA antagonists which are active at the redox site of the NMDA receptor: oxidized and reduced glutathione, PQQ (pyrroloquinoline quinone), compounds that generate nitric oxide (NO) or other oxidation states of nitrogen monoxide (NO+,NO−) such as nitroglycerin and derivatives, sodium nitroprusside, and other NO generating agents, nitric oxide synthase (NOS) inhibitors e.g., Arginine analogs including N-mono-methyl-L-arginine (NMA), N-amino-L-arginine (NAA), N-nitro-L-arginine (NNA), N-nitro-L-arginine methyl ester, N-iminoethyl-L-ornithine, flavin inhibitors: diphenyliodinium, calmodulin inhibitors, trifluoperizine, calcineurin inhibitors, e.g., FK-506 (inhibits calcineurin and thus NOS diphosphorylase). Other non-competitive NMDA antagonists may also be used, e.g, 831917189 (Hoechst-Roussel; Somerville, N.J.) and Carvedilol (Smith Kline Beecham; Philadelphia, Pa.). In addition to antagonists which act at the NMDA receptor, inhibitors of events downstream from activation of the NMDA receptor, e.g., agents which inhibit protein kinase C activation by NMDA stimulation (involved in NMDA toxicity), may be used: MDL 27,266 (Marion-Merrill Dow; Kansas City, Mo.) and triazole-one derivatives, monosialogangliosides (e.g. GM1 from Fidia Corp., Italy) and other ganglioside derivatives, LIGA20, LIGA4 (may also effect calcium extrusion via calcium ATPase). Also included are agents which inhibit downstream effects from receptor activation to decrease phosphatidylinositol metabolism, such as kappa opioid receptor agonists: U50488 (Upjohn; Kalamazoo, Mich.) and dynorphan, kappa opioid receptor agonist, PD117302 CI-977 or agents which decrease hydrogen peroxide and free radical injury, e.g., antioxidants, 21-aminosteroid (lazaroids) such as U74500A, U75412E and U74006F, U74389F, FLE26749, Trolox (water soluble alpha tocopherol), 3-5-dialkoxy-4-hydroxybenzylamines, compounds that generate nitric oxide (NO) or other oxidation states of nitrogen monoxide (NO+, NO−). The methods of the invention also include the use of agents active at the metabotropic glutamate receptor such as agents that block the receptor, e.g., AP3 (2-amino-3-phosphonoprionic acid), or agents that act as agonists of the receptor, e.g., (1S, 3R)-1-Amino-cyclopentane-1,3-dicarboxylic acid [(1S,3R)-ACPD], commonly referred to as 'trans'-ACPD. Also included are agents that decrease glutamate release, e.g., adenosine and derivatives such as cyclohexyladenosine, CNS1145, conopeptides: SNX-111, SNX-183, SNX-230, omega-Aga-IVA, toxin from the venom of the funnel web spider, and compounds that generate Nitric Oxide (NO) or other oxidation states of nitrogen monoxide (NO+,NO) as described above. Also included are agents that decrease intracellular calcium following glutamate receptor stimulation, such as agents to decrease intracellular calcium release, e.g., dantrolene (sodium dantrium), Ryanodine (or ryanodine+caffeine) or agents that inhibit intracellular calcium-ATPase, e.g., Thapsigargin, cyclopiazonic acid, BHQ ([2,5-di-(tert butyl)-1,4-benzohydroquinone; 2,5-di-(tert-butyl)-1, 4benzohydroquinone].

The protective agent may also be a calcium channel blocker, such as one that reduces an ethambutol-induced rise in intracellular calcium. Preferably, the calcium channel blocker does not destroy the chemotherapeutic activity of the drug with which it is co-administered. More preferably, the calcium channel blocker is capable of crossing the blood-brain barrier, and most preferably, is capable of contacting the optic nerve, e.g. nimodipine.

The invention also includes a method in which a drug with optic nerve toxicity is coadministered with both an NMDA antagonist and a calcium channel blocker.

DETAILED DESCRIPTION

The drawings will first be briefly described.
Drawings FIG. 1 is a line graph showing dose-dependent toxicity of ethambutol to retinal ganglion cells in vitro. Dissociated rodent retinal ganglion cells were incubated with increasing concentrations of ethambutol for 24 hours. The ability of cells to take up and cleave fluorescein diacetate was used as an index of their viability and lack of injury. Retinal ganglion cells were identified by 1,1'-dioctadecyl-3,3,3',3'-tetramethylindocarbocyanine (DiI) (Molecular Probes, Eugene, Oreg.) fluorescence (retrogradely transported from a prior injection into the superior colliculus). Retinal ganglion cells (open circles) and all other cells (open squares) were scored separately for viability. Retinal ganglion cells were selectively damaged by ethambutol; the half maximal effect was seen at 10 μM ethambutol. (*) indicates statistical difference by an analysis of variance (ANOVA) followed by Scheffe multiple comparison of means, P<0.01. Values were normalized to control (n=1) and represent the means ± standard deviations of four experiments; at least 150 retinal ganglion cells scored for control values in each experiment.

FIG. 2B illustrates a retina from an ethambutol-treated animal and shows loss of cells from the retinal ganglion cell layer (GCL contains both retinal ganglion cells and displaced amacrine cells). No changes were detected in other retinal layers: INL (inner nuclear layer); ONL (displaced amacrine cells)

FIG. 2C is a bar graph showing a quantification of the cell loss shown in FIG. 2B. The ethambutol-treated animals had 18% fewer cells in the retinal ganglion cell layer than control eyes (n=5). (*) indicates statistical difference from control by the Student's t test (p<0.01).

FIG. 3 is a bar graph showing attenuation of ethambutol toxicity by NMDA antagonists. Dissociated retinal cells were incubated with either no added drug, 12 μM dizocilpine (the open channel NMDA antagonist, MK-801), 100 μM APV (the specific NMDA receptor antagonist), 12 μM MEM (an open channel NMDA antagonist), 100 nM nimodipine ("Nimo" a calcium channel blocker) or 100 μM CNQX (a non-NMDA antagonist). As shown by the left six bars, incubation of retinal ganglion cells with drug alone did not affect cell viability. The right bars illustrate cell viability in the presence of 10 μM ethambutol. APV, memantine, nimodipine and MK-801 were observed to protect retinal ganglion cells from ethambutol-mediated toxicity. However, the non-NMDA glutamate antagonist, CNQX, was ineffective at preventing ethambutol-mediated cell death at the concentration tested. Values are normalized to control (n=1) and represent the means ± standard deviations of four experiments; at least 150 cells scored for control values in each experiment. (*) indicates statistical difference by an analysis of variance (ANOVA) followed by Scheffe multiple comparison of means, P<0.01.

FIG. 4 is a bar graph showing prevention of ethambutol toxicity by enzymatic degradation of endogenous glutamate. Approximately half of the retinal ganglion cells incubated with 10 μM ethambutol died within 24 hours compared to sibling control cultures. Treatment with glutamate-pyruvate transaminase (GPT) in the presence of the cosubstrate sodium pyruvate, or treatment with either compound alone, had no effect on retinal ganglion cells. To inactivate GPT, it was heat treated (HT). This preparation of the enzyme plus pyruvate did not block ethambutol toxicity. In the presence of ethambutol, neither GPT (in the absence of pyruvate) or pyruvate alone saved retinal ganglion cells from ethambutol toxicity. In contrast, when GPT was administered in the presence of pyruvate in order to degrade the endogenous glutamate, 10 μM ethambutol no longer injured retinal ganglion cells. (*) indicates statistical difference by an analysis of variance (ANOVA) followed by Scheffe multiple comparison of means, P<0.01.

FIG. 5 is a bar graph showing prevention of ethambutol toxicity by exogenous administration of $Zn^{2+}$. Dissociated retinal cells were incubated with either no added drug, 10 µM ethambutol (Eth), 100 µM $ZnCl_2$, or both ethambutol and $Zn^{2+}$. $Zn^{2+}$ protected retinal ganglion cells from ethambutol-mediated toxicity. Values were normalized to control (n=1) and represent the means ± standard deviations of four experiments; at least 150 cells were scored for control values in each experiment. (*) indicates statistical difference by an analysis of variance (ANOVA) followed by Scheffe multiple comparison of means, P<0.01.

FIG. 6 is a bar graph showing the effect of ethambutol and $Zn^{2+}$ on the cellular response to NMDA. Dissociated retinal ganglion cells were labeled with the calcium sensitive dye, fura-2. 100 µM NMDA were then applied by puffer, and the peak intracellular calcium concentration measured (peak response occurred between 10 and 70 seconds after NMDA exposure for all cells). The indicated drugs were then applied in the following concentrations: 10 µM ethambutol (Eth) or 100 µM $Zn^{2+}$. Values are means ± standard deviations. Ethambutol + NMDA led to a 20% greater rise in intracellular calcium then NMDA alone. (*) indicates statistical difference by an analysis of variance (ANOVA) followed Scheffe multiple comparison of means, P<0.01. Ethambutol, NMDA, and $Zn^{2+}$ simultaneously led to the same rise seen with NMDA alone. Ethambutol alone or in combination with $Zn^{2+}$ had no effect under these conditions.

Mechanisms of Optic Neuritis

It has now been discovered that drug-induced optic neuritis is due to NMDA receptor-mediated glutamate excitotoxicity. Glutamate-mediated cell damage and cell death appears to underlie both idiopathic and drug-induced retinal cell damage.

Certain drugs, e.g., ethambutol, have toxic side effects resulting in visual impairment or loss. This toxicity is now known to be mediated through the NMDA receptor. For example, ability of the antibiotic drug, ethambutol, may render retinal cells susceptible to NMDA-mediated glutamate damage by chelating endogenous $Zn^{2+}$. The results described below demonstrate that NMDA antagonists and calcium channel blockers are effective protective agents which reduce or prevent retinal cell damage.

Drug-Induced Optic Neuritis

In addition to ethambutol, a number of other drugs cause optic neuritis which may result in visual impairment and loss. The methods of the invention have been shown to be effective in preventing retinal cell damage induced by the drugs, ethambutol, 5-FU, deferoxamine, and tamoxifen. Since these drugs are structurally unrelated, it is likely that the methods of the invention protect retinal cells by acting on a common event or pathway downstream of drug binding, i.e., NMDA receptor-mediated glutamate excitotoxicity of retinal ganglion cells.

Idiopathic Optic Neuritis

The cause or mechanism of the majority of non-drug-induced optic neuritis is unknown. Clinical changes, e.g, retinal cell damage, observed in non-drug-induced optic neuritis are identical to those observed in drug-induced cases of optic neuritis. These observations strongly suggest that non-drug-induced and drug-induced optic neuritis cause cell damage or death via the same or similar mechanisms. Thus, the methods of the invention can also be efficacious in protecting retinal cells from damage in non-drug-induced optic neuritis.

The role of glutamate in optic neuritis:

Glutamate toxicity to the retina primarily affects the inner retinal layers, especially the retinal ganglion cell layer. It has now been discovered that the toxicity of certain drugs, e.g., ethambutol, and glutamate toxicity are likely to be mediated through similar mechanisms. The predominant form of in vitro glutamate excitotoxicity of retinal ganglion cells is mediated by over-stimulation of the N-methyl-D-aspartate (NMDA) subtype of glutamate receptor, which in turn leads to excessive levels of intracellular calcium.

The role of glutamate in ethambutol toxicity

Ethambutol kills retinal ganglion cells both in culture and in the whole animal. Ethambutol-induced cell death is similar to that seen with toxic levels of glutamate indicating that ethambutol toxicity is mediated through the NMDA receptor via an "excitotoxic" mechanism.

Glutamate, by binding to the NMDA receptor on retinal ganglion cells, leads directly to a rise in intracellular calcium. As discussed below, there is no such effect with ethambutol alone. If the endogenous glutamate is eliminated from in vitro retinal ganglion cell culture conditions, then ethambutol is no longer toxic to retinal ganglion cells. These data indicate that ethambutol makes these cells more sensitive to endogenous glutamate, and that ethambutol is not a direct agonist at the NMDA receptor. It has now been discovered that NMDA antagonists are efficacious at preventing ethambutol-mediated retinal ganglion cell loss. Accordingly, the invention provides methods of reducing antibiotic toxicity by administering agents that can block glutamate mediated "excitotoxicity", e.g., NMDA antagonists and calcium channel blockers.

The role of zinc in ethambutol toxicity

Ethambutol is toxic to retinal ganglion cells because of its ability to chelate endogenous zinc. Ethambutol appears to deplete endogenous levels of zinc. This depletion renders the cell—which would ordinarily be immune to endogenous levels of glutamate—now more sensitive to low levels of this excitatory amino acid.

$Zn^{2+}$ is known to play a significant role in glutamate neurotransmission. $Zn^{2+}$ is known to modulate all pharmacological subtypes of ionotropic glutamate receptors, as well as NMDA receptors (Hollman, M., Boulter, J., et al., 1993, Neuron 110: 943–954). It has been well documented that, at high concentrations, $Zn^{2+}$ inhibits NMDA mediated toxicity. $Zn^{2+}$ has also been shown to potentiate agonist-induced currents in certain splice variants of the NMDA receptor (Hollman, 1993, supra). However, this mechanism has not been demonstrated or suggested in the retina.

Experiments were performed to study the role of zinc in ethambutol toxicity. Zinc supplementation was observed to block any toxic effects of ethambutol in cell viability assays.

Exposure of cells to NMDA led directly to a rise in intracellular calcium. When ethambutol and NMDA were applied simultaneously to retinal ganglion cells, an even greater rise in intracellular calcium was observed compared to the rise seen with NMDA alone. Ethambutol and $Zn^{2+}$, alone or in combination, had no effect on the level of intracellular calcium. Ethambutol, zinc, and NMDA, administered simultaneously, had the same effect as NMDA alone on intracellular calcium. These experiments suggested that ethambutol increases the sensitivity of the retinal ganglion cell to NMDA, and that this increased sensitivity is intimately associated with endogenous zinc.

These data suggested that the administration of exogenous $Zn^{2+}$ could protect retinal ganglion cells from ethambutol toxicity. However, oral zinc supplementation abrogates ethambutol's chemotherapeutic effect on TB, making the drug effectively useless. The present invention provides methods of reducing ethambutol toxicity while preserving the chemotherapeutic activity of the antibiotic. NMDA antagonists can protect retinal ganglion cells from ethambutol toxicity while preserving ethambutol's anti-mycobacterial activity. Thus, the invention provides a promising clinical approach to reducing antibiotic toxicity.

Role of ethambutol in the TB and AIDS epidemics:

*Mycobacterium tuberculosis* is an obligate parasite infecting humans, other primates in contact with humans, and other mammalian species in close contact with humans, especially domestic dogs and cats. However, humans are the only reservoir of the organism. *M. tuberculosis* is an aerobic, non-spore-forming, non-motile bacillus. Other mycobacteria that cause disease in AIDS patients are *M. kansasii, M. xenopi, M. cheloni, M. gordonae,* and *M. bovis* (Mandell, G. L., Douglas, R. G., et al., 1990, *Churchill Livingstone:* 1074).

Ethambutol is a mainstay in the treatment of tuberculosis in both the AIDS and general populations (MMWR, 1993, *Morbidity & Mortality Weekly Report* 42: 961–4; and MMWR, 1993, *Morbidity & Mortality Weekly Report* 42: 1–8). Ethambutol is likewise a mainstay in the treatment of *Mycobacterium avium,* a second major pathogen in the AIDS population.

Mycobacteria take up ethambutol rapidly when the drug is added to cultures that are in the exponential growth phase. However, because the drug is tuberculostatic, growth is not significantly inhibited before 24 hours. Although the precise mechanism of action of ethambutol is unknown, the drug has been shown to inhibit the incorporation of mycolic acid into the mycobacterial cell wall.

As both the TB and HIV epidemics worsen, ethambutol will continue to be a critical chemotherapeutic agent in the treatment of mycobacterial disease. In addition to the potentially devastating visual loss that may occur with ethambutol therapy, even reversible visual loss may present a major clinical problem, i.e, patient compliance. Chemotherapy for tuberculosis is generally prescribed for extended periods; patients experiencing visual impairment as a consequence of such therapy are less likely to complete the course of treatment. Partial or incomplete compliance is a major factor in the development of drug-resistant strains of pathologic mycobacteria. If this side effect can be prevented without compromising the chemotherapeutic efficacy of ethambutol, this would both improve both patient compliance and quality of life. If visual loss resulting from ethambutol treatment can be reduced or prevented, both patient compliance and the quality of life for afflicted individuals will be improved.

The experiments described below suggest the following: 1) Ethambutol is toxic to retinal ganglion cells both in vitro and in vivo. This toxicity develops at concentrations one might expect in the ocular tissues of humans undergoing ethambutol therapy for TB or other mycobacterial infections. 2) Ethambutol toxicity is blocked by NMDA antagonists and calcium channel blockers, but not by non-NMDA glutamate antagonists. 3) Ethambutol toxicity is dependent upon the presence of endogenous glutamate. These results suggest that ethambutol increases the sensitivity of retinal ganglion cells to glutamate at the NMDA receptor.

Regardless of the exact mechanism by which ethambutol is toxic to retinal ganglion cells, the NMDA antagonists and calcium channel blockers described function effectively as protective agents. The invention provides novel and promising methods of preventing ethambutol toxicity in AIDS and TB patients.

NMDA antagonists as protective agents

Protective agents likely to be efficacious in reducing antibiotic toxicity may be classified according to their method of action. Table 1 lists competitive NMDA antagonists which act as an agonist at the NMDA binding site, e.g., APV. Table 2 lists uncompetitive NMDA antagonists, e.g., MK-801 and memantine. Tables 3–12 list other NMDA antagonists likely to be useful in the treatment of optic neuritis.

Advantages

Protective agents administered to patients to treat drug-induced optic neuritis must not interfere with the therapeutic action of the primary drug. Although one can identify pharmacologic agents that can block the side effects of ethambutol, it cannot be at the expense of ethambutol's antimicrobial efficacy. Experiments described herein demonstrate that the claimed methods effectively reduce damage to retinal cells without destroying the chemotherapeutic activity of the antibiotic. In vitro experiments demonstrate that memantine and other NMDA antagonists added to cells at the same time as ethambutol were found to be effective protective agents.

Another major advantage is that many of these drugs, e.g., memantine and nimodipine, can be administered systemically with little toxicity. Many of these drugs have been well characterized and are currently used as therapeutic agents. MK-801 (dizocilpine), an open channel NMDA blocker, is one of the best characterized NMDA antagonists unknown. The calcium channel blocker, nimodipine, has the advantage of having current clinical approval for other indications. Nimodipine has also been shown to attenuate NMDA toxicity. Memantine, which is presently used in Europe for the treatment of Parkinson's disease, has limited toxicity and is likely to be superior to MK-801 in clinical use.

Superiority of memantine as an NMDA antagonist:

Memantine is well tolerated clinically and is an NMDA open-channel blocker and uncompetitive antagonist (Chen, H. S. V., Pelligrini, J. W., et al., 1992, *J. Neurosci.* 12: 4424–4436).

Memantine (1-amino-3,5-dimethyladamantane hydrochloride), known to have anti-Parkinsonian (Schwab, R. S., England, A. J., et al., 1969, *JAMA* 208: 1168), and anti-epileptic (Meldrum, B. S., Turski, L., et al., 1986, *Naunyn Schmiedebergs Arch Pharm* 332: 93) properties, is an analog of amantadine (1-adamantanamine hydrochloride), a well-known anti-viral agent that has been used clinically for over 20 years in the U.S.A. (Schneider, E., Fischer, P. A., et al., 1984, *Dtsch Med Wochenschr* 109: 987).

Memantine appears to be safer than MK-801 because of unique rapid-response kinetics, allowing substantial residual NMDA receptor function even in areas of potentially damaged neurons (Chen, 1992, supra). Low micromolar concentrations levels of memantine are therapeutic and well tolerated in Parkinson's disease (Wesemann, W., Sontag, K.

H., et al., 1983, *Arzneimittelforschung*, 33: 1122). Memantine has been used for Parkinson's disease in Europe for the past decade.

The voltage and agonist-dependency of memantine are consistent with a mechanism of uncompetitive inhibition and open-channel block. Pharmacologically, uncompetitive antagonism is defined as inhibition by the antagonist that is contingent upon prior activation of the receptor by the agonist. In this case, open-channel block is a type of uncompetitive inhibition in which the NMDA receptor-operated ion channels must open before the blocking agent can move into the voltage-field of the pore and effectively block the channel. It is believed that the blocking site of memantine is inside the channel pore, close to or interacting with the $Mg^{2+}$ binding site.

Since memantine is an uncompetitive open channel blocker, the degree of blockade increases with increasing concentrations of agonist (Chen, 1992, supra). Thus, any important advantage of memantine is the greater the toxic load of glutamate, the more efficacious memantine may be at protecting neurons. In the face of glutamate excitotoxicity, the proportion of current inhibited by memantine actually increases; yet, a basal level of NMDA-evoked response remains. Compared with other NMDA open-channel blockers, including ketamine, phencyclidine, and tricyclic antidepressants, the faster kinetics of action of low micromolar memantine, coupled with a Ki of ~1–2 µM at the resting potential make this drug ideal for the prevention of NMDA-related neurotoxicity.

It has now been discovered that memantine inhibits NMDA-evoked $[Ca^{2+}]i$ responses. Using digital calcium imaging techniques, 6 µM memantine was observed to largely prevent the excessive influx of calcium elicited by 200 µM NMDA. In fact, $[Ca^{2+}]i$ rose only to levels associated with a low degree of NMDA receptor stimulation in the presence of memantine. This result further supports the premise that memantine allows basal NMDA receptor-mediated responses but blocks excessive NMDA-evoked activity.

In vivo, memantine is clinically tolerated as long as the concentration remains near the Ki. When used according to the invention, it functions as an open-channel blockade during periods of potential NMDA-mediated glutamate toxicity. At a given concentration of memantine, the effects of high concentrations of NMDA were blocked to a relatively greater degree than low concentrations.

Human Dosage and Administration

The methods of this invention are useful in treating any mammal, including humans.

According to this invention, mammals are treated with pharmaceutically effective amounts of a protective agent alone or a protective agent in conjunction with another drug, e.g., ethambutol, for a period of time sufficient to reduce optic neuritis. Ethambutol is typically administered orally; protective agents co-administered with ethambutol may be delivered orally or by any other appropriate means of delivery described below or known in the art.

In accordance with this invention, pharmaceutically effective amounts of a protective agent can be administered alone to treat optic neuritis. Alternatively, a protective agent may be administered sequentially or concurrently with another drug, e.g., ethambutol. The most effective mode of administration and dosage regimen of protective agent and drug will depend upon the type of disease to be treated, the severity and course of that disease, previous therapy, the patient's health status, and response to drug and the judgment of the treating physician. Generally, a protective agent should be administered to a patient in a dose to achieve serum or intravitreal concentration of 0.1 nM to 100 mM.

Preferably, the protective agent and drug are administered simultaneously or sequentially with the protective agent being administered before, after, or both before and after treatment with the drug. Conventional modes of administration and standard dosage regimens of protective agents, e.g., glutamate antagonists, can be used. Optimal dosages for co-administration of a drug with a protective agent can be determined using methods known in the art. Dosages of protective agents may be adjusted to the individual patient based on the dosage of the drug with which the agent is co-administered and the response of the patient to the treatment regimen. The protective agent may be administered to the patient at one time or over a series of treatments.

Agents that cannot cross the blood/brain barrier, e.g., memantine, dizocilpine, APV, may be administered locally, e.g., intravitreally, topically, or intrathecally. Agents capable of crossing the blood/brain barrier, e.g., nimodipine, can be administered systemically, e.g., orally, intravenously.

The compositions used in these therapies may also be in a variety of forms. These include, for example, solid, semi-solid, and liquid dosage forms, such as tablets, pills, powders, liquid solutions or suspension, liposomes, suppositories, injectable and infusible solutions. The preferred form depends on the intended mode of administration and therapeutic application. The compositions also preferably include conventional pharmaceutically acceptable carriers which are known to those of skill in the art.

Efficacy and dosages of the protective agents discussed herein can be evaluated using the rodent model of ethambutol-induced retinal ganglion cell loss. The starting dosage of a protective agent, i.e., NMDA antagonist, and antibiotic can be initially determined in vitro. Data from these studies can be used to determine appropriate dosing regimens for human administration. Initially, 0.1–1000 µM MK-801, 0.1 to 1000 µM memantine, and 0.1 to 1000 nM nimodipine can be tested in vitro against various concentrations of ethambutol in cell viability experiments. This will allow for selection of optimal in vivo concentrations.

Once an appropriate concentration of, for example, nimodipine, is determined that can prevent retinal ganglion cell loss in vitro, minimum inhibitory concentration evaluations both in the presence and absence of this concentration of nimodipine can be determined to insure that the anti-microbial efficacy of ethambutol (and other anti-mycobacterial agents) is preserved.

In vivo experiments using the rat model of ethambutol toxicity can be carried out as follows. Ethambutol is administered orally to Long Evans rats at a daily dose of 100 mg/kg. Control animals receive vehicle only. After between two and four months, the animals are sacrificed, and the eyes enucleated. The optic nerves and chiasm are analyzed separately. All retinas are prepared as whole mounts, and Nissl stained according to established protocols. Focusing on the ganglion cell layer, the cells in each retina are counted in a masked fashion using an upright microscope equipped with a 40× objective. All positively stained cells within the field of the eyepiece reticule are included. Sample fields are taken at 0.25 µM intervals along the temporal, nasal, ventral and dorsal axes from the optic nerve to the retinal periphery. Forty fields are analyzed for each retina. This precludes the variable of different retinal ganglion cell densities in different areas of the retina.

Figure 2A:
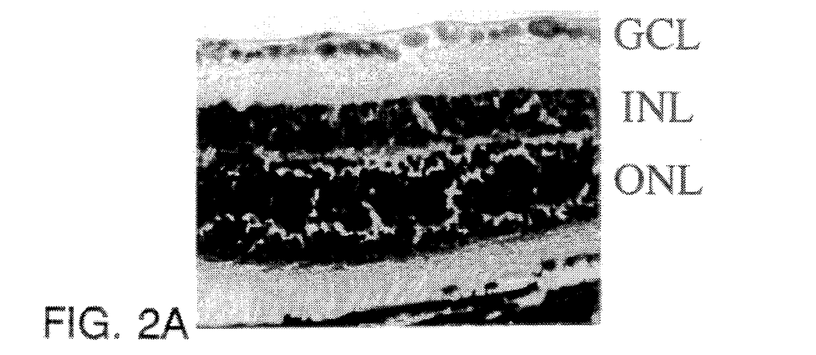
FIGS. 2A and 2B are photographs of stained tissue sections showing ethambutol toxicity to retinal ganglion cells in vivo. Rats were administered ethambutol for 30 days at a daily dose of 100 mg/kg. Control animals were administered vehicle alone. After thirty days, the animals were sacrificed, and the eyes enucleated. Both tissue sections and Nissl stained whole mounts were prepared. A control retina is shown in FIG. 2A.

To more easily detect the protective effects of NMDA antagonists or nimodipine, the severity of the retinal ganglion cell loss in vivo can be increased. For example, if approximately 30% retinal ganglion cell loss can be obtained with ethambutol administration, this will simplify testing of antagonists. Longer or shorter durations of treatment can also be evaluated. For example, ethambutol can be administered to rats for 2–4 months, rather than the one month illustrated in FIG. 2A–2C, followed by evaluation of retinal tissue. Nimodipine, memantine or MK-801 can be administered simultaneously or sequentially with ethambutol. The animals are then sacrificed, and the retinas evaluated as described above.

In addition, N-(6-methoxy-8-quinolyl)-p-toluenesulfonamide (TSQ, Molecular Probes, Eugene, Oreg.) can also be used in these preparations to test whether chronic ethambutol administration results in a depletion of zinc from retinal ganglion cells. Staining techniques with TSQ and can be utilized both to assess zinc in ethambutol treated subjects, and in those subjects that have received both ethambutol together with a protective agent.

Some NMDA antagonists have a well-documented ability to interfere with normal neuronal function, both in vitro and in vivo (Lipton, S. A. and Rosenberg, P. A., 1994, *N Eng J Med* 330: 613–622). Unwanted toxic side effects from the administration of NMDA antagonists can be readily detected in in vitro assays in which a given agent's ability to prevent ethambutol's toxicity to retinal ganglion cells is screened in culture. Such assays are simple and far quicker than whole animal studies. Prior to human administration, however, in vivo studies using the art-recognized rat model are carried out to confirm the in vitro toxicity studies. Such routine toxicity evaluations are well within the skill of the art.

Two agents, nimodipine and memantine, are particularly well tolerated in humans. A number of other NMDA antagonists, such as the anticonvulsant drug, 2-phenyl-1,3-propanediol dicarbamate (felbamate), and many of the agents listed in Tables 1–12, are currently in clinical use and can be used as protective agents. The assays described above can also be used to identify additional NMDA antagonists that can protect retinal ganglion cells from ethambutol toxicity.

The antibiotic and protective agent may be administered in any manner which is medically acceptable, e.g., combined with any non-toxic, pharmaceutically-acceptable carrier substance suitable for administration to animals or humans. In some cases, it may be advantageous to administer the antibiotic and protective agent in combination with other anti-mycobacterial drugs. For example, a protective agent may be administered either simultaneously or sequentially with another therapeutic agent, e.g., one or more antibiotics or one or more antiinflammatory drugs to treat the underlying infection. Combination therapy may also allow administration of a lower dose of each drug, thus lessening potential side effects of therapy associated with high doses of either drug alone.

Evaluation of optic neuritis in vitro and in vivo

The rat is an art-recognized model for the evaluation of ethambutol toxicity. Lessell and others explored the toxic effect of ethambutol administration in rats. Lesions were identified in the optic nerves and chiasm marked predominately by "focal dilatation of axons" (Lessell, S., 1976, *Investigative Ophthalmology & Visual Science* 15(9): 765–9). The eyes were not evaluated in this study. Other investigators have explored ethambutol induced lesions in various animal models; to date, however, there are no descriptions of the ophthalmic histopathology (Trentini,G. P., Botticelli, A., et al., 1974, *Virchows Archiv A Pathological Anatomy & Histopathology* 362(4): 311–14),; Wolf, R. H., Gibson, S. V., et al., 1988, *Laboratory Animal Science* 38(1): 25–33).

Long-Evans or Sprague Dawley CD rats were used for in vivo studies as a source of rat retinal cells for in vitro experiments.

Rats, aged postnatal day P2-P10 were utilized to harvest neurons for cell culture. The rats, of either sex, were housed in litters of 10 pups to a lactating adult female.

During the injection of fluorescent dyes to retrogradely label the retinal ganglion cells, the animals were anesthetized and any necessary incisions only made if the animal is unconscious and unresponsive. Anesthesia is selected appropriate to the age of the animal. The injection itself was performed with a fine needle which was carefully inserted through the soft bone tissue. The incision was then closed with fine sutures and the animal resuscitated in a warm, oxygen-rich environment. The entire procedure usually lasts 5 minutes and the pups are promptly returned to their mothers. The animals show no signs of discomfort and behave normally within 20 minutes.

For the harvest of retinal cells for cultures, the animals are killed by cervical dislocation after the induction of $CO_2$ narcosis or cryoanesthesia. Adult rats were also anesthetized by $CO_2$ narcosis before sacrifice.

Postnatal rat retinal ganglion cells were cultured using methods well known in the art. Briefly, retinal ganglion cells of four-to-six day old Long-Evans rats were retrogradely labeled with DiI. NMDA responses were present in acutely dissociated and cultured retinal ganglion cells of this age. The rat pups were injected under anesthesia with DiI in the superior colliculus; the dye was then retrogradely transported to retinal ganglion cells (the only retinal cells with projections to the superior colliculus). Two to six days after injection, the animals were sacrificed by decapitation. Following enucleation, the retinas were dissociated with mild papain treatment. The retinal cells were then plated onto glass cover slips coated with poly-L-lysine in 35 mm tissue culture dishes. The growth medium routinely used was Eagle's minimal essential medium supplemented with 0.7% (w/v) methylcellulose, 0.3% (w/v) glucose, 2 μM glutamine, 5% (v/v) rat serum, and 1 μg/ml gentamicin. Retinal ganglion cells were identified by the presence of the retrogradely transported DiI. Viable cells were scored by their ability to take up and cleave fluorescein diacetate to fluorescein. Acutely isolated retinal ganglion cell neurons were cultured for 24 hours with 10 μM ethambutol and each of the following drugs: memantine, MK-801, APV, and nimodipine.

Fluorescence imaging was also used to follow cellular physiology with respect to ethambutol induced toxicity, and the role played by NMDA receptor-mediated neurotoxicity.

Neuronal intracellular free $Ca^{2+}$ concentration ($[Ca^{2+}]i$) was analyzed with fura-2 acetoxymethyl ester (fura 2-AM; Molecular Probes) following procedures known in the art. DiI labeled retinal ganglion cells were subsequently labeled with fura-2. Agonists (NMDA-glycine, glutamate, etc.) were applied by pneumatic pipettes (aperture ~10 mm, 3–6 psi) placed 10–20 μm from the cells of interest. Data were analyzed via the Metamorph software package (Image 1).

The $Zn^{2+}$ sensitive fluorescent dye, N-(6-methoxy-8-quinolyl)-p-toluenesulfonamide (TSQ, Molecular Probes, Eugene, Oreg.) can also be used in dissociated retinal ganglion cell preparations in the presence and absence of ethambutol, to measure changes in intracellular $Zn^{2+}$ concentration as a consequence of ethambutol treatment.

Another fluorescent probe, mag-fura-2 (Molecular Probes, Eugene, Oreg.), can be used to monitor cytosolic $Mg^{2+}$ concentrations in vitro. Direct measurement of changes in $Mg^{2+}$ concentrations can be made by monitoring sister cultures under identical conditions with mag-fura-2, instead of fura-2 or TSQ. Free $Zn^{2+}$ can also be measured utilizing mag-fura-2. The peak in the mag-fura-2 excitation spectrum occurs at 323 nm for $Zn^{2+}$, and at 335 nm for $Mg^{2+}$. This allows for the simultaneous measurement of both cytosolic $Zn^{2+}$ and $Mg^{2+}$ in the same cell and the ability to separate the effects of ethambutol on cytosolic zinc from any effects on $Mg^{2+}$.

The examples which follow identify and describe (a) the cells damaged, (b) the mechanism of cell loss, and (c) agents that block this toxic side effect of ethambutol. The efficacy of the methods of the invention in reducing antibiotic toxicity is also demonstrated in vitro and in vivo.

EXAMPLE 1

Ethambutol is toxic to retinal ganglion cells in vitro:

Initial experiments were carried out in vitro. Freshly dissociated rat retinal preparations were exposed to increasing concentrations of ethambutol. These experiments established that 50% or more of the retinal ganglion cells were killed when exposed to 10 μM ethambutol for 24 hours in culture. Retrograde transport of the fluorescent dye DiI was used to label retinal ganglion cells. The dye was injected into the superior colliculus of four day old (P4) rat pups. The only cells in the retina with projections to the colliculus are the retinal ganglion cells; accordingly, these are the only cells that demonstrate DiI fluorescence when retinas from these injected animals are evaluated. The eyes were enucleated from P6–P10 animals, and the retinal tissue dissociated. Retinal cells were incubated in the presence of increasing concentrations of ethambutol, and scored for viability at 24 hours. Retinal ganglion cells were identified by the presence of DiI fluorescence.

Figure 1:
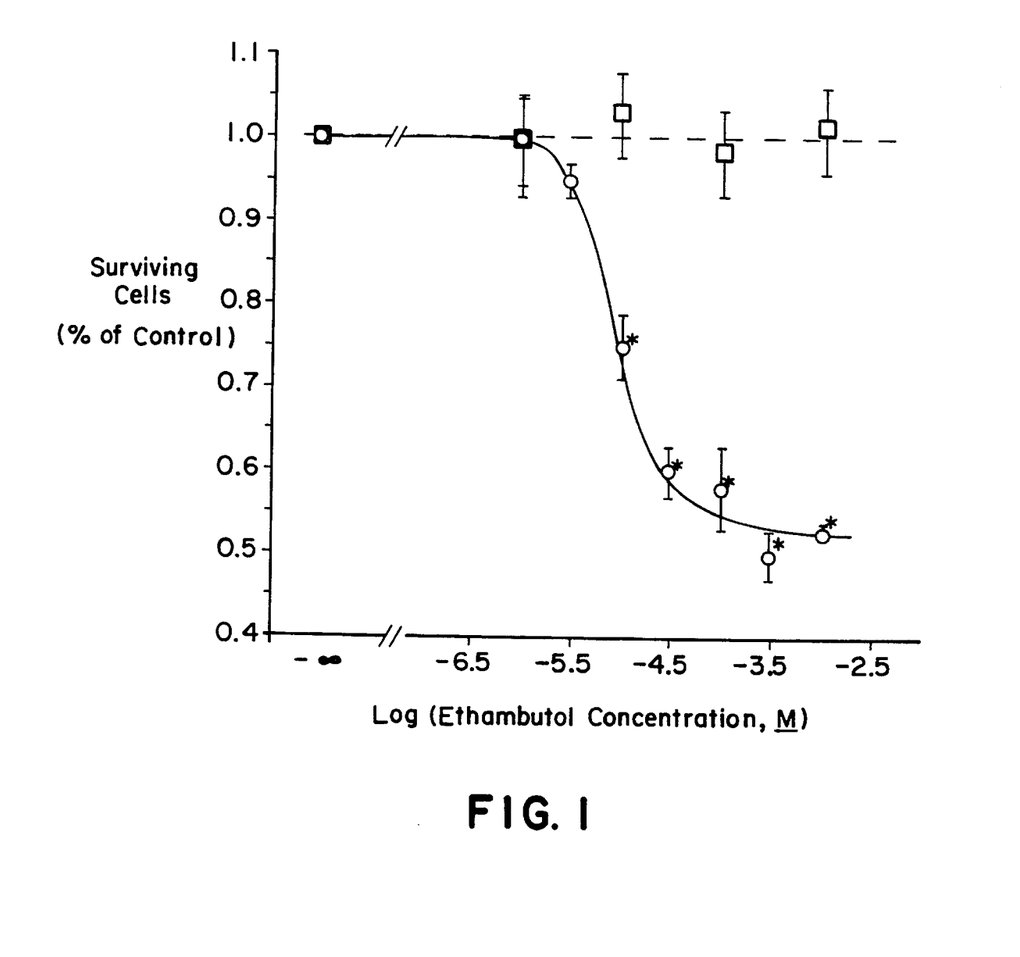

Viability was assayed by uptake and cleavage of a second fluorescent dye, fluorescein diacetate. Ethambutol toxicity was detected only in retinal ganglion cells (FIG. 1, open circles). No ethambutol toxicity was noted in any other cell type in these preparations (FIG. 1, open squares). Fluorescein diacetate uptake was not specific for any cell type, and was observed to be taken up and cleaved by most viable cells in these preparations. Accordingly, the relative "health" of the other cell types in the retinal dissociations could be assayed. The selective toxicity of ethambutol to retinal ganglion cells has been confirmed in vivo (described below).

Furthermore, as shown in FIG. 1, ethambutol is toxic to retinal ganglion cells in a dose dependent fashion; the half maximal effect is seen at approximately 10 μM. This is of significant for the following reasons. Gundert and coworkers had previously found a concentration of 10 μM ethambutol in the cerebrospinal fluid of patients taking the drug orally (Gundert, 1972; Gundert, R. U., Klett, M., et al., 1973, *European J. of Clinical Pharmacology* 6(2): 1973. Gundert, R. U., Weber, E., et al., 1972, *Verhandlungen der Deutschen Gesellschaft fur Innere Medizin* 78(1564): 1564–7). Similar concentrations were also identified in the eyes of experimental animals administered ethambutol. Thus, 10 μM ethambutol is within the range of ethambutol concentration to which the optic nerve and retinal ganglion cells are exposed in patients taking ethambutol for chronic antimycobacterial therapy.

EXAMPLE 2

In vivo toxicity Of ethambutol

Figure 2B:
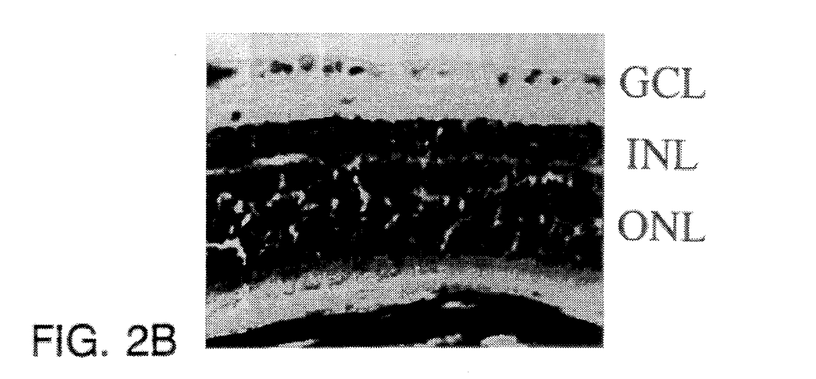
Figure 2C:
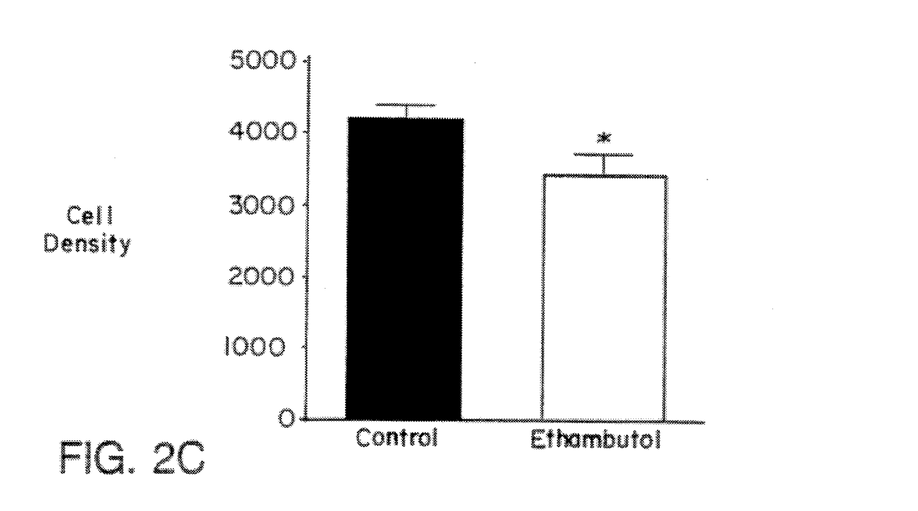

Ethambutol toxicity to retinal ganglion cells was confirmed in vivo. Long-Evans rats were administered ethambutol orally for 30 days at a daily dose of 100 mg/kg. After thirty days, the animals were sacrificed, and the eyes enucleated. As shown in FIG. 2B–2C, ethambutol resulted in the loss of 18% of the retinal ganglion cells; no other ocular pathology was detected. Analysis of the optic chiasm and the optic nerve revealed histopathological changes characteristic of ethambutol toxicity. These in vitro and in vivo results therefore suggest that the visual compromise seen as a consequence of ethambutol therapy is a result of a direct effect on retinal ganglion cells.

EXAMPLE 3

NMDA antagonists inhibit drug toxicity

Having established that ethambutol is toxic to retinal ganglion cells, strategies to reduce or block antibiotic-mediated cell loss were explored. The data suggested that ethambutol toxicity was relatively selective. The only pathologic changes found both in vitro and in vivo were to retinal ganglion cells.

Figure 3:
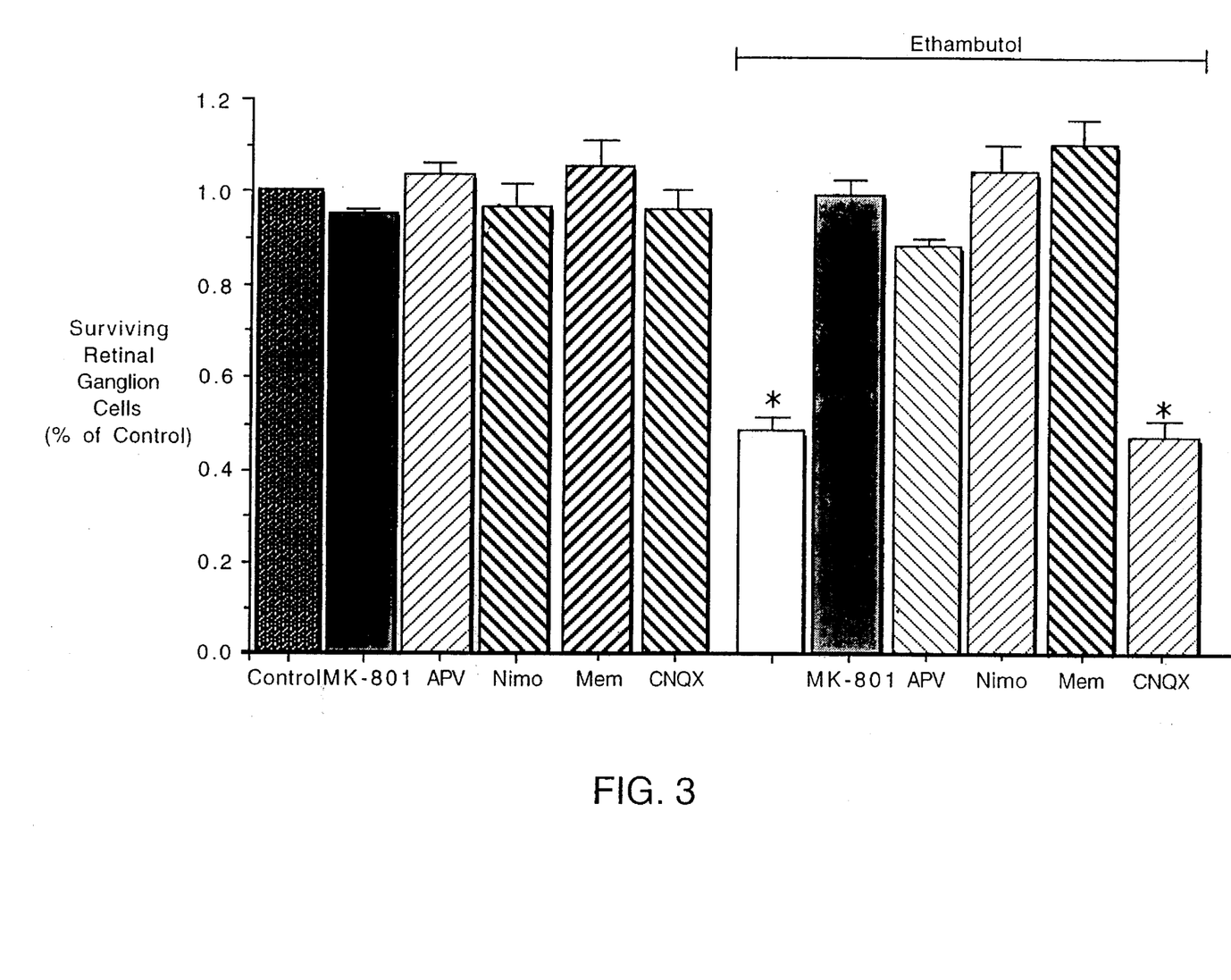

This suggested that glutamate excitotoxicity was implicated in ethambutol mediated cell loss. Accordingly, NMDA antagonists and/or calcium channel blockers were tested for the ability to block ethambutol toxicity. As shown in FIG. 3, NMDA antagonists and calcium channel blockers prevented the retinal ganglion cell loss associated with ethambutol treatment. The left four bars represent treatment of control cultures with either no added drug, dizocilpine (the open channel NMDA antagonist, MK-801), APV (the specific NMDA receptor antagonist 2-amino-5-phosphonovalerate), the open channel NMDA blocker, memantine, or the calcium channel antagonist, nimodipine. As shown by the left four bars of FIG. 3, these drugs have no effect on retinal ganglion cell viability alone. As shown in the right bars, however, these drugs protect retinal ganglion cells from ethambutol.

Although, as noted above, glutamate can bind to a variety of receptors on retinal ganglion cells, its toxic effects appear to be predominantly mediated through the NMDA receptor. To confirm that ethambutol toxicity was mediated through the NMDA receptor, viability studies were performed with non-NMDA glutamate antagonists. As shown in FIG. 3, the non-NMDA antagonist, 6-cyano-7-nitroquinoxaline-2,3-dione (CNQX) was ineffective at preventing ethambutol-mediated cell death. It is possible that CNQX and other members of this class of protective agents may require a higher concentration to protect retinal cells. This is in contrast to the NMDA antagonists, APV, MK-801, memantine, and the calcium channel blocker, nimodipine which (as were discussed above) do protect retinal ganglion cells from ethambutol induced injury.

Figure 8:
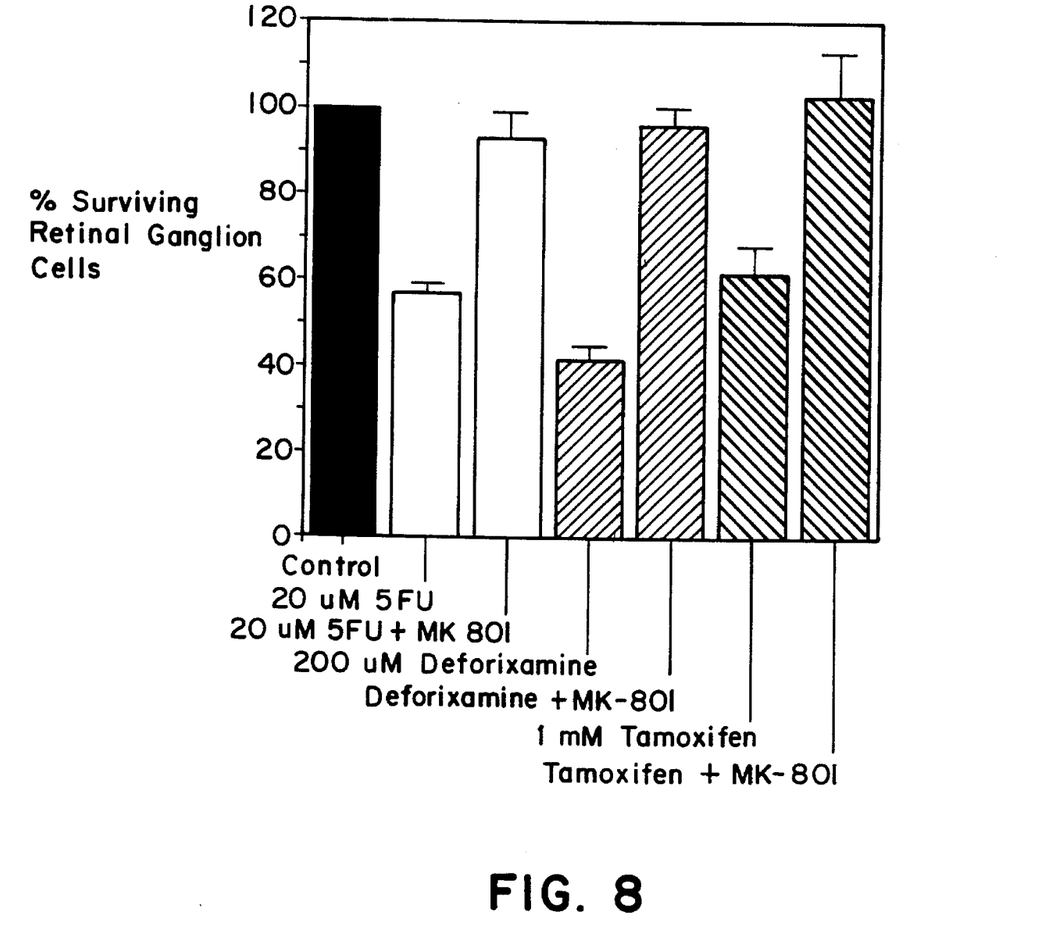
FIG. 8 is a bar graph showing prevention of drug toxicity by the protective agent, MK801. The drugs, are all toxic to retinal ganglion cells. Retinal ganglion cells were incubated for 24 hours with either drug alone (5-fluorouracil (5-FU), Defororixamine, and Tamoxifenor drug +MK801, followed by measurement of cell viability.

As discussed above, other drugs are known to cause optic neuropathy (see Table 13). However, the mechanism of drug toxicity has not been defined. Experiments were carried out to determine whether NMDA antagonists prevented retinal cell damage induced by such drugs. As shown in FIG. 8, the drugs, 5-FU, Defororixamine, and Tamoxifen were all found to be toxic to retinal ganglion cells. The cytotoxic effect of these drugs on retinal ganglion cells was prevented by the NMDA antagonist, MK801. The data suggest that optic neuritis induced by structurally-unrelated drugs, e.g., drugs listed in Table 13, is mediated by a direct action on retinal ganglion cells. These data also indicate that this cytotoxicity is mediated through the NMDA receptor, and that the methods of the invention can be used to prevent or reduce drug-induced retinal cell damage and optic neuritis.

EXAMPLE 4

Endogenous glutamate is necessary for ethambutol toxicity

The role of endogenous glutamate in ethambutol toxicity was evaluated. Endogenous glutamate in retinal cultures was 26±2 µM (mean ±standard deviation, n=12) (as measured by high pressure liquid chromatography).

Figure 4:
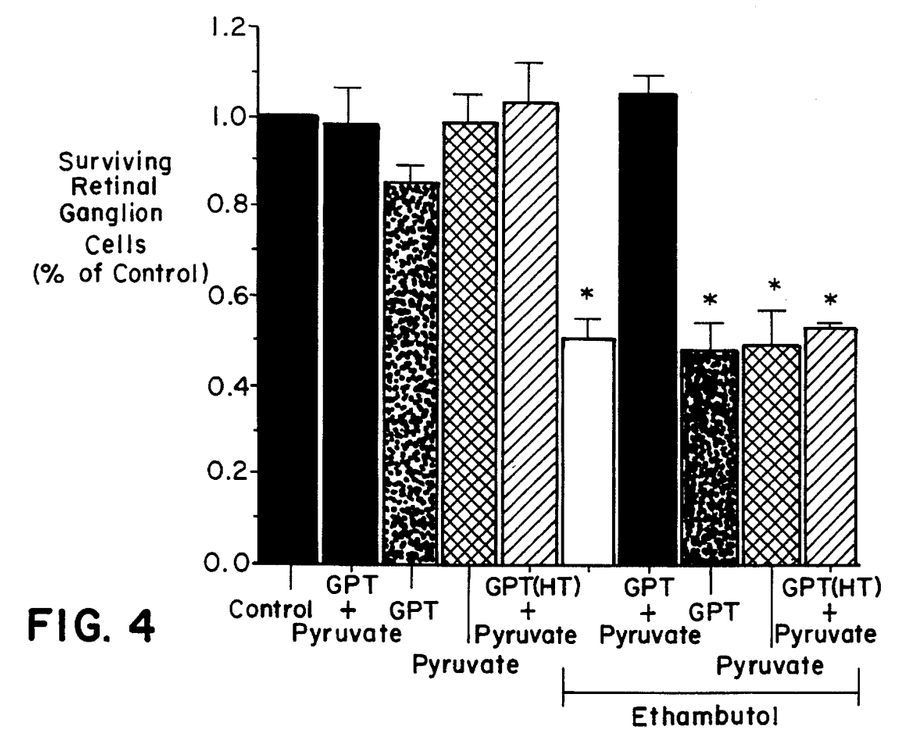

This level of endogenous glutamate was not affected by overnight incubation with ethambutol. Under standard cell culture conditions, this amount of glutamate has been shown to be relatively non-toxic to retinal ganglion cells. Nevertheless, experiments were carried out to determine whether endogenous glutamate was required for the expression of ethambutol toxicity in these preparations. FIG. 4 shows the results of such an experiment. The endogenous glutamate was specifically degraded by the addition of the enzyme glutamate-pyruvate transaminase (GPT) in the presence of the cosubstrate pyruvate. This treatment resulted in a decrease in the endogenous glutamate levels to 7±1 µM (n=4) as measured by HPLC analysis. Under these conditions, ethambutol was no longer toxic to retinal ganglion cells. Heat treatment (HT) of the enzyme, or incubation of the cultures with either GPT or pyruvate alone did not protect the retinal ganglion cells from ethambutol toxicity. Thus, these data strongly suggest that ethambutol toxicity to retinal ganglion cells requires the presence of endogenous glutamate.

There are several possible explanations for the finding that ethambutol toxicity to retinal ganglion cells is mediated through the NMDA receptor. A primary effect of NMDA is its known ability to increase intracellular calcium in neurons; this effect was monitored via the fluorescent dye, fura 2. Accordingly, dissociated retinal ganglion cells were labeled with fura-2. Ethambutol in concentrations from 1 nM to 1 mM was puffed onto retinal ganglion cells for periods of up to five minutes. No change was detected in 25 of 25 cells examined. As a control, 100 µM NMDA was subsequently puffed onto these cells, and in 23 of 25 cells the intracellular calcium rose to 300 µM or higher. These data together with the observation that endogenous glutamate is essential for ethambutol-mediated cell death suggest that it is unlikely that ethambutol functions simply as an agonist at the NMDA receptor.

EXAMPLE 5

The role of zinc in ethambutol toxicity

As discussed above, $Zn^{2+}$ is known to play a significant role in glutamate neurotransmission. $Zn^{2+}$ has been proposed as a regulator of glutamate receptors in certain brain regions, most notably the mossy fiber system of the hippocampus. It has been well documented that, at high concentrations, $Zn^{2+}$ inhibits NMDA mediated toxicity (Choi, D. W., Weiss, J. H., et al., 1989, *Ann N Y Acad Sci* 568(219): 219–24); Christine, C. W. and Choi, D. W., 1990, *J Neurosci* 10(1): 108–16); Yeh, G. C., Bonhaus, D. W., et al., 1990, *Mol Pharmacol* 38(1): 14–9).

Given that both ethambutol and its oxidation metabolic product (2,2'-(ethylenediimino)-dibutyric acid) chelate $Zn^{2+}$ at physiologic conditions, it is possible that ethambutol can function at the NMDA receptor by chelating—and therefore depleting—the endogenous $Zn^{2+}$ (Cole, A., May, P.M., et al., 1981, *Agents & Actions* 11(3): 296–305). This could then potentiate NMDA mediated excitotoxicity. If ethambutol is chelating endogenous $Zn^{2+}$, this may then allow the endogenous glutamate to adversely effect the retinal ganglion cells.

Figure 5:
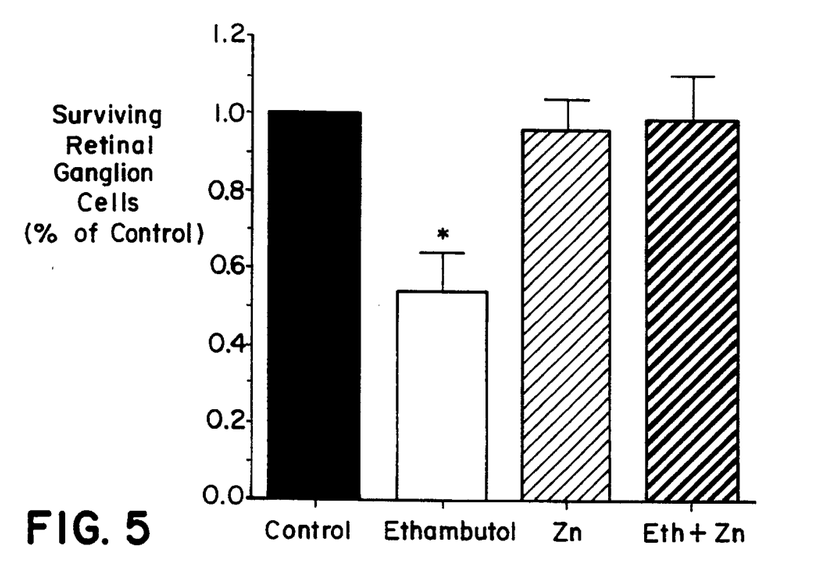

This hypothesis would suggest that the addition of exogenous $Zn^{2+}$ could protect retinal ganglion cells from ethambutol toxicity. In fact, this is indeed the case as shown in FIG. 5. Dissociated retinal cells were incubated with either no added drug, 10 µM ethambutol, 100 µM $ZnCl_2$, or both ethambutol and $Zn^{2+}$. Viability of retinal ganglion cells was determined at 24 hours. As shown above, ethambutol was toxic to retinal ganglion cells; exogenous $Zn^{2+}$, however, blocked this toxicity.

Since a rise in intracellular calcium is one of the neuron's first responses to exogenously applied glutamate or NMDA, the following experiment was performed to detect changes in intracellular calcium. Dissociated retinal ganglion cells were labeled with the calcium sensitive dye, fura 2. Fura 2 allows for measurement of cytosolic calcium concentrations.

Figure 6:
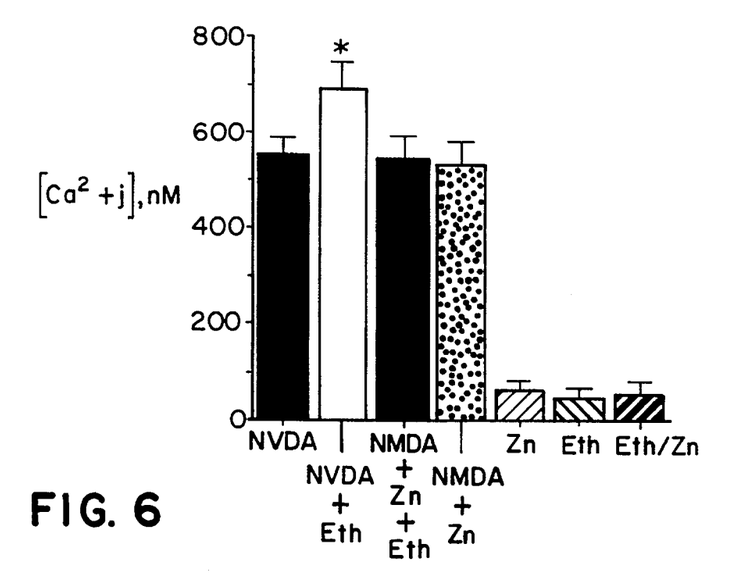

100 µM NMDA was applied to individual retinal ganglion cells, and the rise in intracellular calcium measured. This rise in intracellular calcium is shown in FIG. 6, first bar. The cells were then allowed to recover, and the intracellular calcium returned to baseline. 10 µM ethambutol and 100 µM NMDA were then simultaneously applied to the same cell (FIG. 6, second bar). In 16 of 20 cells, this treatment resulted in at least a 20% greater rise in intracellular calcium, suggesting that ethambutol was increasing the cellular response to NMDA.

As a second experiment, 100 µM $Zn^{2+}$ chloride was added to the ethambutol/NMDA puffer. In the presence of 100 µM $Zn^{2+}$, 100 µM NMDA plus 10 µM ethambutol led to a rise in intracellular calcium that was indistinguishable from NMDA alone (FIG. 6, third bar). 100 µM $Zn^{2+}$ plus 10 µM ethambutol, or either component separately, had no effect on intracellular calcium (10/10 cells each). Accordingly, exogenous $Zn^{2+}$ reduced the NMDA/ethambutol response to the baseline NMDA response.

Figure 7:
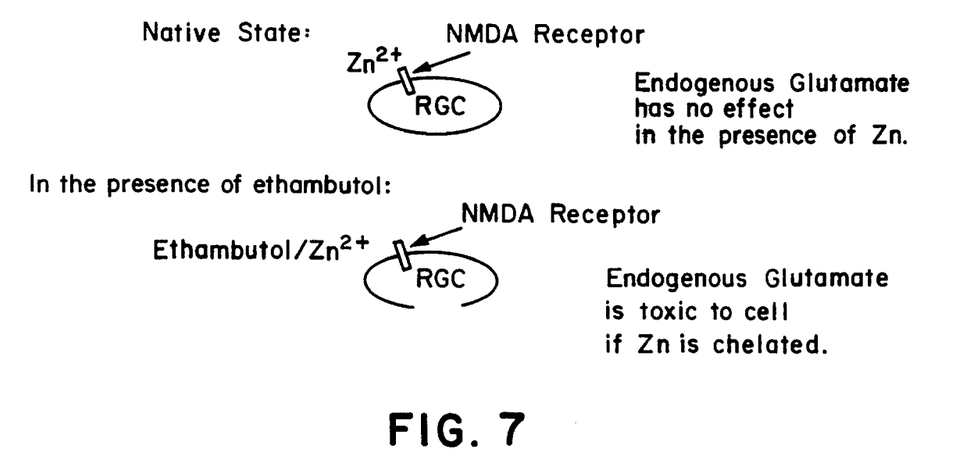
FIG. 7 is a diagram showing the proposed mechanism of the role of ethambutol and $Zn^{2+}$ on the cellular response to NMDA. In the presence of physiologic $Zn^{2+}$, endogenous glutamate is non-toxic to retinal ganglion cells (RGC). However, when the endogenous $Zn^{2+}$ is chelated by ethambutol, this glutamate is now toxic to these cells.

FIG. 7 illustrates a mechanism for ethambutol toxicity to retinal ganglion cells. In the native state, $Zn^{2+}$ serves as a protective agent to prevent endogenous glutamate from exerting a toxic effect on the retinal ganglion cell. When this $Zn^{2+}$ is chelated by ethambutol, the cell is rendered sensitive to the endogenous concentrations of glutamate. If ethambutol further depletes serum $Zn^{2+}$ in patients with already low levels, this may make their retinal ganglion cells more sensitive to endogenous glutamate.

These experiments suggest that $Zn^{2+}$ supplements—administered orally—might protect patients from the toxic side effects of ethambutol. Unfortunately, this is an unacceptable solution because zinc supplementation significantly decreases the ethambutol's antibiotic activity against TB.

EXAMPLE 6

Preservation of antimicrobial efficacy

The following experiments were performed in vitro to insure that the NMDA antagonists or calcium channel blockers discussed above do not interfere with ethambutol's toxicity to mycobacteria.

Mycobacterium sensitivity to antibiotic preparation in the presence and absence of NMDA antagonists were evaluated. Eleven *M. tuberculosis* and eight *M. avium* isolates were obtained from AIDS patients (Infectious Disease Unit, Massachusetts General Hospital) for evaluation. Minimal inhibitory concentrations of ethambutol for each strain were obtained by the radiometric Bactec technique (Siddiqi, S., Heifets, L., et al., 1993, *J. of Clinical Microbiology* 31(9): 2332–8). High concentrations of ethambutol were necessary to achieve an anti-microbial effect for several resistant strains of mycobacteria. These ethambutol values were then re-evaluated for each strain in the presence of 100 μM $Zn^{2+}$, 12 μM memantine, 12 μM MK-801, 100 μM APV, and 100 nM nimodipine. Memantine, MK-801, APV and nimodipine had no effect on the concentration of ethambutol necessary to kill the various mycobacterial strains. Similar testing was performed for several other anti-mycobacterial chemotherapeutic agents, and no untoward effect on efficacy was detected. These data indicate that memantine, MK-801, APV and nimodipine did not compromise the ability of ethambutol to kill mycobacteria under these conditions. These results suggest that these agents can be used to control any side effects of ethambutol without compromising ethambutol's anti-microbial action $Zn^{2+}$, however, abrogated the chemotherapeutic effect of ethambutol on all but one strain of mycobacteria tested. $Zn^{2+}$ appears to interfere with the chemotherapeutic effect of ethambutol. Given the known $Zn^{2+}$ chelating effect of ethambutol, it is possible that a $Zn^{2+}$ -ethambutol complex is formed, and that this complex is no longer effective anti-microbial agent.

In vitro sensitivity studies have not indicated that any of the agents tested are likely to pose a problematic decrease in chemotherapeutic activity of ethambutol or any other anti-mycobacterial agent. Although the radiometric Bactec technique used to determine the minimum inhibitory concentrations is an excellent predictor of in vivo sensitivity, the possibility does exist for unforeseen drug interactions, particularly in the treatment of *Mycobacterium avium* infections. Drug interactions can be evaluated using the "beige mouse" model of mycobacterial infections as well as other in vitro and in vivo assays known in the art.

TABLE 1

| Competitive NMDA Antagonists (act at agonist binding site) |
|---|
| CGS-19755 CIBA-GEIGY), D-2-amino-7-phosphonoheptanoate (AP7) |
| CPP {[3-(2-carboxypiperaxin-4-y-propyl-1-phosphonic acid]} |
| LY 274614,CGP39551, CGP37849, LY233053,LY233536 |
| O-phosphohomoserine |

TABLE 1-continued

| Competitive NMDA Antagonists (act at agonist binding site) |
|---|
| MDL100,453 |

TABLE 2

| Channel Blockers (Un-Competitive NMDA Antagonists) |
|---|
| Dextrorphan, caramiphen, rimcazole |
| Ketamine, Tiletamine |
| Phencyclidine (PCP) |
| Phencyclidine (PCP) |
| Amantadine, rimantadine |
| CNS 1102 |
| Diamines |
| Conantokan peptide |
| Agatoxin-489 |

TABLE 3

| Antagonists at Glycine Site of the NMDA Receptor |
|---|
| Indole-2-carboxylic acid |
| DNQX |
| CNQX, NBQX |
| P-9939 |

TABLE 4

| Polyamine Site of NMDA Receptor |
|---|
| Arcaine |
| Ifenprodil |
| Diethylenetriamine SL 82,0715 |
| 1,10-diaminodecane |

TABLE 5

| Redox Site of NMDA Receptor |
|---|
| Oxidized and reduced glutathione |
| PQQ (pyrroloquinoline quinone) |
| Nitroglycerin, Sodium Nitroprusside |
| N-mono-methyl-L-arginine (NMA); N-amino-L-arginine (NAA); N-nitro L-arginine (NNA); N-nitro-L-arginine methyl ester, N-iminoethyl-L-ornithine |
| Diphenyliodinium; trifluoperizine |
| FK-506 |

TABLE 6

| Other Non-Competitve NMDA Antagonists |
|---|
| 831917189 |
| Carvedilol |

TABLE 7

Agents to inhibit protein kinase C
activation by NMDA stimulation
(involved in NMDA toxicity)

MDL 27,266
GM1 LIGA20, LIGA4

TABLE 8

Downstream effects from Receptor Activation

U50488
U50488 dynorphan
PD117302, CI-977
U74500A, U75412E and U74006F
U74389F, FLE26749, Trolox
Nitroglycerin, Sodium Nitroprusside
N-mono-methyl-L-arginine (NMA);
N-amino-L-arginine (NAA); N-nitro-
L-arginine (NNA); N-nitro-L-arginine
methyl ester; N-iminoethyl-L-
ornithine

TABLE 9

Non-NMDA antagonists

CNQX, NBQX, YM900, DNQX,
PD140532
AMOA (2-amino-3[3-
9carboxymethoxyl-5-
methoxylisoxaxol-4-yl]propionate]
2-phosphophonoethyl phenylalanine
derivatives, i.e. 5-ethyl, 5-methyl, 5-
trifluoromethyl
GYK152466
Evans Blue

TABLE 10

Agents Active at Metabotropic
Glutamate Receptors

AP3 (2-amino-3-phosphoprionic
acid)
(1S, 3R)-1-Amino-cyclopentane-1,3-
dicarboxylic acid [(1S,3R)-ACPD],
'trans'-ACPD

TABLE 11

Agents to decrease glutamate release

Adenosine, e.g.,cyclohexyladenosine
CNS1145
Conopeptides: SNX-111,SNX-183,
SNX-230
Omega-Aga-IVA, toxin from venom
of funnel web spider

TABLE 12

Drugs to decrease intracellular
calcuim following glutamate receptor
stimulation Dantrolene (soduim dantrium);
Ryanodine (or ryanodine + caffiene)
Thapsaigargin, cyclopiazonic acid,
BHQ ([2,5-di(tert butyl)-1,4-
benxohydroquinone; 2,5-di-(tert-
butyl)-1,4benxohydroquinone]

TABLE 13

| | |
|---|---|
| Amantidine | Iodopyracet |
| Amiodarone | Isoniazid |
| Amoproxan | Khat |
| Antipyrine | Lead |
| Arsenicals | Lysol |
| Aspidium | Methanol |
| Barbiturates | Methotrexate |
| Caramiphen hydrochloride | Methyl acetate |
| Carbon disulfide | Methyl bromide |
| Carbon tetrachloride | Octamoxin |
| Carmustine | Oil of chenopodium |
| Chloramphenicol | Oral contraceptives |
| Chlorodinitrobenzene | Penicillamine |
| Chlorpromazine | Pheniprazine |
| Chlorpropamide | Plasmocid |
| Cobalt chloride | Quinine |
| Deferoxamine | Sodium fluoride |
| Dinitrobenzene | Streptomycin |
| Dinitrotoluene | Sulfonamides |
| Disulfiram | Tamoxifen |
| Ergot | Thallium |
| Ethambutol | Thioglycolate |
| Ethchlorvynol | Tin |
| Ethyl alcohol | Tolbutamide |
| Favism | Toluene |
| 5-Fluorouracil | Trichloroethylene |
| Halogenated hydroxyquinolines | Tricresyl phosphate |
| Hexachlorophene | Vincristine |
| Iodoform | Vinylbenzene |

What is claimed is:

1. A method of treatment or propylaxis of optic neurtitis in a mammal suffering from or at risk of developing drug-induced optic neuritis, said method comprising administering to said mammal a protective agent which inhibits glutamate-mediated retinal cell damage.

2. The method of claim 1, wherein said drug chosen from the drugs listed in Table 13.

3. The method of claim 1 wherein said protective agent is a N-Methyl-D-aspartate (NMDA) antagonist.

4. The method of claim 3, wherein said NMDA antagonist is an uncompetitive open channel blocking agent.

5. The method of claim 4, wherein said agent is memantine.

6. The method of claim 4, wherein said agent is dizocilpine.

7. The method of claim 4, wherein said agent is chosen from the agents listed in Table 2.

* * * * *